United States Patent
Bossard et al.

(10) Patent No.: US 9,518,904 B2
(45) Date of Patent: Dec. 13, 2016

(54) SYSTEM AND METHOD OF QUANTIFYING IMPURITIES MIXED WITHIN A SAMPLE OF HYDROGEN GAS

(71) Applicants: Peter R. Bossard, Ivyland, PA (US); Luis Breziner, Ivyland, PA (US); Paolo Moreschini, Lansdale, PA (US)

(72) Inventors: Peter R. Bossard, Ivyland, PA (US); Luis Breziner, Ivyland, PA (US); Paolo Moreschini, Lansdale, PA (US)

( * ) Notice: Subject to any disclaimer, the term of this patent is extended or adjusted under 35 U.S.C. 154(b) by 232 days.

(21) Appl. No.: 14/320,729

(22) Filed: Jul. 1, 2014

(65) Prior Publication Data

US 2014/0311220 A1    Oct. 23, 2014

Related U.S. Application Data

(63) Continuation-in-part of application No. 13/314,175, filed on Dec. 7, 2011, now Pat. No. 8,875,559.

(51) Int. Cl.
| | |
|---|---|
| *G01N 7/10* | (2006.01) |
| *C01B 3/50* | (2006.01) |
| *G01N 33/00* | (2006.01) |
| *G01N 1/40* | (2006.01) |

(52) U.S. Cl.
CPC ............... *G01N 7/10* (2013.01); *C01B 3/501* (2013.01); *G01N 1/4005* (2013.01); *G01N 33/005* (2013.01)

(58) Field of Classification Search
CPC ..................................... G01N 7/10; G01N 7/12
See application file for complete search history.

(56) References Cited

U.S. PATENT DOCUMENTS

| | | | | |
|---|---|---|---|---|
| 3,638,396 A | * | 2/1972 | Lovelock | G01N 30/84 73/23.35 |
| 3,718,434 A | * | 2/1973 | Pierce | G01N 7/10 422/83 |
| 4,442,353 A | * | 4/1984 | Baubron | H01J 49/24 250/281 |
| 5,109,710 A | * | 5/1992 | Newkirk | G01N 30/12 73/23.41 |
| 5,360,467 A | | 11/1994 | Ketkar et al. | |

(Continued)

FOREIGN PATENT DOCUMENTS

JP    2007192704 A    *    8/2007

*Primary Examiner* — Daniel J Colilla
(74) *Attorney, Agent, or Firm* — LaMorte & Associates, P.C.

(57) ABSTRACT

A system and method of taking a sample of hydrogen gas and reducing the hydrogen concentration by a factor greater than $1 \times 10^8$ while increasing the partial pressure of the contaminating gases by a factor greater than 100, so that extremely low levels of contamination can be accurately detected. A sample of hydrogen gas is captured. Only the hydrogen gas is removed leaving all the contaminating gases in the collection chamber. This causes the total pressure of the gas sample within the collection chamber to decrease dramatically since most of the gas was hydrogen. All the contaminants remain in the collection chamber. None are lost through pumping. As such, the concentration of contaminants within the remaining sample increases dramatically. The residual partial pressures of the contaminating gases within the collection chamber and can now be measured by a variety of techniques.

18 Claims, 2 Drawing Sheets

(56) References Cited

U.S. PATENT DOCUMENTS

| | | | | |
|---|---|---|---|---|
| 6,473,175 B1 * | 10/2002 | Malczewski | ....... | G01N 33/0014 |
| | | | | 356/311 |
| 2008/0260587 A1 * | 10/2008 | Coleman | ................ | G01N 30/88 |
| | | | | 422/89 |
| 2012/0291696 A1 * | 11/2012 | Clarke | .................... | C30B 25/14 |
| | | | | 117/88 |

* cited by examiner

SYSTEM AND METHOD OF QUANTIFYING IMPURITIES MIXED WITHIN A SAMPLE OF HYDROGEN GAS

RELATED APPLICATIONS

This application is a continuation-in-part of U.S. patent application Ser. No. 13/314,175, filed Dec. 7, 2011.

BACKGROUND OF THE INVENTION

1. Field of the Invention

In general, the present invention relates to systems and methods for determining the concentration of impurities in a sample of gas. More particularly, the present invention relates to systems that detect the concentration of impurities within a sample of hydrogen gas.

2. Prior Art Description

In industry, there are many applications for the use of pure or ultra pure hydrogen. For instance, there are many fuel cells that require the use of hydrogen as fuel. The hydrogen, however, must be pure or ultra pure. Molecules of carbon monoxide, hydrocarbon gases, ammonia, or sulfur compounds can cause damage to the fuel cell and decrease both the efficiency and the functional life of the fuel cell.

Ultra pure hydrogen is also used in the manufacture of printed circuits. If the hydrogen gas is contaminated even with a small amount of a contaminant, such as water vapor, the operational integrity of the circuits can be compromised.

Traditionally, pure and ultra pure hydrogen gas is generated using a two-stage process. In the first stage, hydrogen gas is separated from a source gas. For example, hydrogen can be extracted from either a hydrocarbon or water. However, the extracted hydrogen gas produced is not pure. Rather, when hydrogen is extracted, the resultant gas is often contaminated with hydrocarbons, sulfur compounds, water vapor and/or other gases. It is for this reason that a second processing stage is used.

In the second processing stage, the extracted hydrogen gas is purified to reduce contaminants to or below the maximum specified. In the art, pure hydrogen is commonly considered to be hydrogen having purity levels of at least 99.95% and ultra pure hydrogen is commonly considered to be hydrogen having purity levels of at least 99.99999%. In the prior art, one of the most common ways to create pure hydrogen gas is to pass the gas through a bed of adsorbent material that strips the contaminants from the gas. One of the most common ways to produce ultra-pure hydrogen is to pass the gas through a hydrogen separator that contains a membrane made of a hydrogen permeable material, such as palladium or a palladium alloy. When the hydrogen gas is exposed to the hydrogen permeable membrane, and the partial pressure of hydrogen is higher on one side of the membrane, the hydrogen passes through the membrane from the side where the partial pressure of hydrogen is higher to side to the hydrogen lower pressure is lower. The contaminants do not pass. The hydrogen that passes through the membrane, therefore, becomes purified and is collected for use.

Even after hydrogen gas is purified and collected, there are many ways that the purified gas can again become contaminated. The purifier being used may fail and start to pass impure hydrogen. Furthermore, downstream piping may be contaminated causing the gas to become impure as it passes through the piping. The purifier or downstream piping may also develop leaks due to ware, material defects, ground movements and/or many other reasons. In critical applications, where the purity of the hydrogen gas must be maintained, the application must be monitored for small absolute changes in gas purity before the impurities become large enough to degrade the process and or product.

If a manufacturer does not continuously monitor the purity of the pure or ultra pure hydrogen being used, a contaminant leak could destroy fuel cells, ruin microcircuit production, or otherwise cause harm to a product or manufacturing process. In order to prevent such damage from occurring, many manufacturers periodically or continuously measure the level of contaminants in the ultra pure hydrogen and apply statistical process controls to the collected data to predict when a hydrogen purifier needs to be replaced. In order for statistical process controls to be effectively used, very small increases in contaminants need to be detected and tracked.

In the prior art, pure hydrogen and ultra pure hydrogen are typically tested for purity using a gas chromatograph, a Fourier transform infrared (FTIR) detector, gas chromatography (GC) with a variety of detectors, or a mass spectrometer. In all of these techniques any sample of hydrogen gas can have 4 orders of magnitude more hydrogen than the harmful contamination that is to be measured. By the time the sample is ready for analysis, the amount of contaminants may be reduced so significantly that the contaminants may not be quantifiable.

Contaminants can be concentrated by removing some of the hydrogen in a collected sample using a hydrogen permeable membrane. Ultrapure helium can then be added as the carrier gas to transport the contamination to an appropriate detection device. Such a system is exemplified in U.S. Pat. No 5,360,467 to Katkar. However, the concentrated sample must be carried to the measurement device with an ultrapure stream of helium. The helium has its own contamination levels, that need to be separated from the contamination originally in the hydrogen stream. The contamination at this point, after adding helium as a carrier gas, still makes up a very small fraction of the gas stream to be analyzed. The partial pressure of the contamination gases, such as CO and $H_2S$, make up a very small portion of the gas sample, typically less than 1 part per million.

With the increasing popularity of fuel cell technology, many small companies now have the need to test for contaminants in hydrogen gas. For example, some gasoline stations now provide hydrogen gas as fuel for fuel cell powered cars. By regulation, the hydrogen gas must be periodically tested for purity. Such testing must be outsourced to labs because there are no techniques available to measure the carbon monoxide and sulfur contaminations on site. Lab results take time to receive. Accordingly, a gas station may be selling contaminated gas for days, weeks or months before the problem can be detected due to degradation of the fuel cell. The targeted useful life of an automobile fuel cell is greater than ten years if the hydrogen is used for the fuel cell always meets the purity requirements. The dynamic range of an instrument meeting this need will be approximately six orders of magnitude in terms of impurity concentrations across gas types with a resolution for each contamination gas of approximate 1% of the maximum allowed impurity level.

A long standing need, therefore, exists for a system that can sample hydrogen gas and quantify various contaminating gases with widely ranging contamination levels in a simple and cost effective manner. This need is met by the present invention as described and claimed below.

SUMMARY OF THE INVENTION

The present invention is a system and method of determining a concentration of impurities in a gas sample that is mostly hydrogen. A hydrogen separator is provided having a gas sample collection space and a diffusion space that are separated by a hydrogen permeable membrane. The hydrogen gas permeates through the hydrogen permeable membrane. The rate that the hydrogen permeates thru the membrane is measured over time which allows the total hydrogen sample taken to be quantified. This provides a method of calculating the molar volume of hydrogen to better than one percent with the total volume of hydrogen contained in the instrument at any time to approximately ten cubic centimeters. When the sample has been collect and isolated more than 99.9999% of the total hydrogen in the gas sample will be removed leaving the contamination gases as the bulk of the remaining gases. To remove this percentage of hydrogen, it is first purge with nitrogen or removed with a vacuum pump. This lowers the partial pressure of hydrogen in the collection space to the low millitorr range. Most of the remaining hydrogen in the collection is eliminated my sweeping a reactive gas across the outer surface of the membrane that is in the hydrogen diffusion space. The hydrogen atoms on the surface of the membrane are now removed as in a combustion reaction that enables the partial pressure of the hydrogen in the collection space to be reduced to less than a millitorr.

The contaminants now can have partial pressures that are significantly higher than the residual hydrogen pressure. In addition, the absolute value of the partial pressures of the contamination have been increase because the volume they are now contained in is a between 20 and 1000 times smaller than the sample volume size. The hydrogen concentration in the sample is typically reduced by a ratio greater than $1 \times e^7$. If the hydrogen sample has low levels of contamination the sensitivity can be measure in the low parts per trillion range.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system and method can be configured in many alternate ways, only one exemplary embodiment of the system is illustrated. The exemplary embodiment is selected in order to set forth one of the best modes contemplated for practicing the invention. However, the shown embodiment is exemplary and is not intended to be a limitation upon the scope of the present invention as defined by the appended claims.

Figure 1:
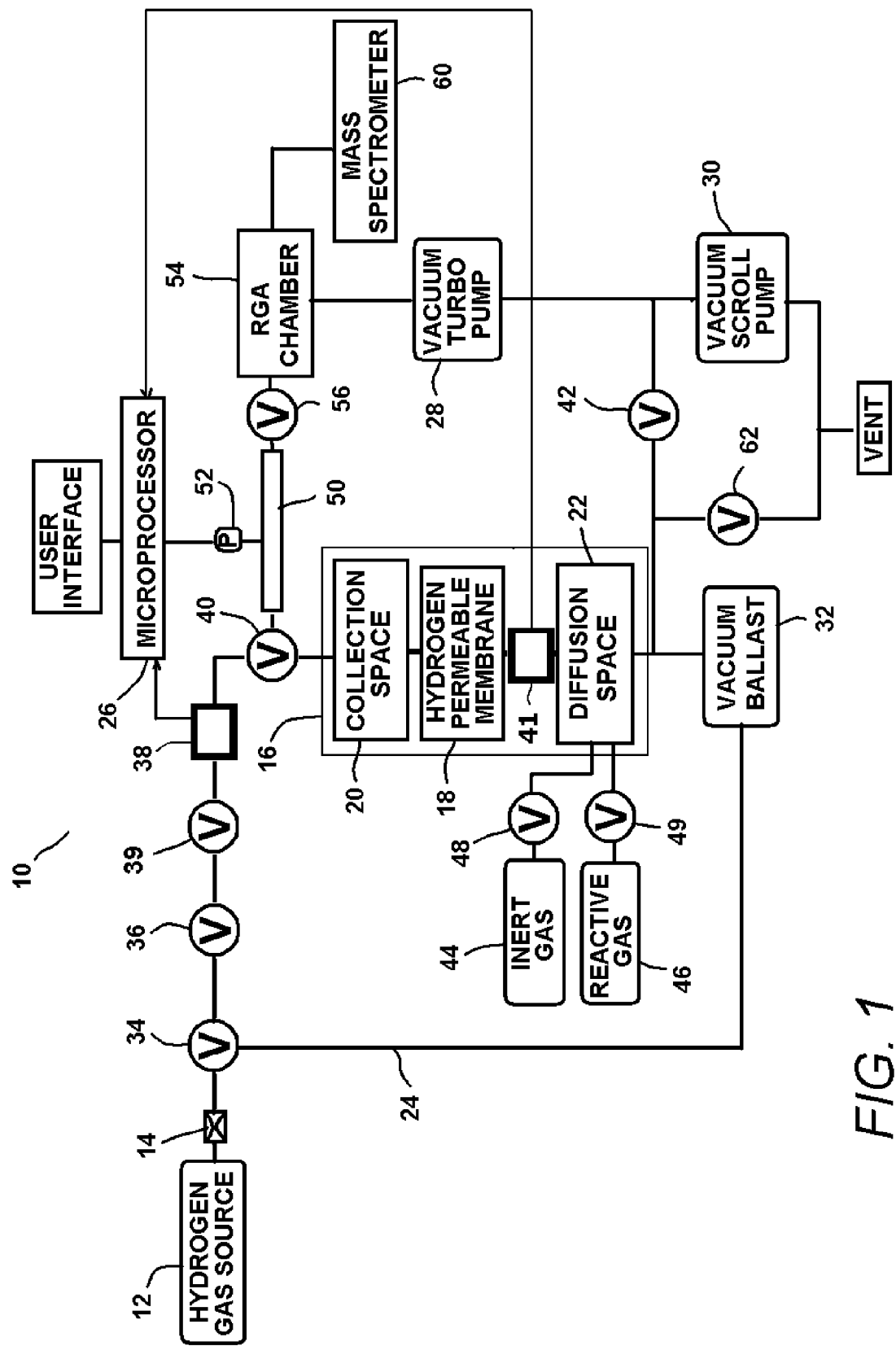
FIG. 1 is a block diagram schematic of an exemplary embodiment of a contamination detection system in accordance with the present invention.

Referring to FIG. 1, a schematic of a contamination level detection system 10 is illustrated. The contamination level detection system 10 takes a sample of hydrogen gas from a high pressure hydrogen gas source 12, such as a hydrogen gas storage tank at a neighborhood gas station. The pressure of the sample is lowered. This is achieved using a low pressure tap, a gas restrictor, or similar pressure reducing device 14.

The contamination level detection system 10 utilizes a first hydrogen separator 16. The hydrogen separator 16 utilizes a hydrogen permeable membrane 18 that is made of a palladium alloy. The hydrogen permeable membrane 18 separates the impurities from the hydrogen as the hydrogen passes thru the palladium membrane. A mass flow meter is used to measure the rate that the hydrogen passes thru the hydrogen permeable membrane 18 as a function of time. This gives the total volume of the hydrogen sample. The hydrogen separator 16 is heated to its operating temperature between 60 and 600 degrees Celsius using heaters (not shown).

With the hydrogen removed from the collection volume, the contaminating gases are directed toward and away from the hydrogen separator 16 using an evacuated network 24 of tubes and valves. An ultra-pure source of hydrogen as the carrier gas for the GC column, is generated from a second palladium cell 74 using the same hydrogen that is being tested for purity. Ultra pure hydrogen flow rates are in the single digit cc per minute. The operations of the various valves are controlled by a microprocessor 26. The flow of gases through the network 24 is also controlled by the use of a vacuum turbo pump 28, and a vacuum scroll pump 30.

The collection space 20 of the hydrogen separator 16 receives the gas sample that has been reduced in pressure. A MFM (Mass Flow Meter) 38 is used to measure the standard volume of the hydrogen sample that used in the analysis. This has three significant advantages. First, the size of the sample is unrestricted and determined by the measured mass flow rate as a function of time. Second, the maximum volume of hydrogen in the system at any time is a small number. Third, the volume of the overall system's plumbing can be reduced.

The volume of the collection space 20 is small, preferably between 1 cc and 20 cc. However, other volumes can be used. It will be understood that the separate valves 34, 36, 39 shown can be substituted with multiple position rotary valves. The use of separate valves is used to help simplify the description of operational parameters.

With the hydrogen separator 16 running at its operating temperature, a fifth valve 42 is opened to vent the diffusion space 22 of the hydrogen separator 16 to the atmosphere. Although not illustrated, check valves are used where appropriate to assure gas flow in only the directions desired. As the gas sample reacts with the hydrogen permeable membrane 18, hydrogen gas begins to diffuse from the collection space 20 and thru a mass flow meter 41 in order to quantify the amount of hydrogen taken in the sample. As the hydrogen gas diffuses through the hydrogen permeable membrane 18, any impurities mixed with the gas sample remain within the collection space 20. As the hydrogen gas diffuses out of the collection space 20, the concentration of impurities in the collection space 20 increases by the ratio of the volume of sample hydrogen that has passed thru through the hydrogen permeable membrane 18 divided by the volume of the collection space 20. Depending on the sample size this ratio is typically between 50 and 1000. The sample size is determined by optimizing the time the measurements will take along with the sensitivity required for quantifying the impurities to the required level.

The diffusion space 22 of the hydrogen separator 16 is coupled to both an inert gas source 44 and a reactive gas source 46. The inert gas source 44 is preferably a nitrogen source However, other gases that do not react with hydrogen can be used. It should also be noted that a vacuum source and be used instead of the inert gas source 44 for purging lines. The reactive gas source 46 is preferably a source of air or any other gas mixture having free oxygen that will react with the hydrogen at the operating temperature of separator 16 and not leave residual material in the diffusion space 22.

After the diffusion space 22 is vented for a period of time, when the desired sample size of hydrogen is collected, valve 40 is closed. A sixth valve 48 is opened and the diffusion space 22 is swept with the inert gas from the inert gas source 44. This drops the partial pressure of hydrogen in the collection space 22 from approximately 760 Torr (1 atm) down to approximately one Torr in a short time. As a direct consequence, the concentration of impurities as a percentage of remaining gas increases within the collection space 22. The increase in concentration is proportional to the change in partial pressure of the hydrogen in the collection space 22. As a result, impurities by volume percentage of gas increase by a factor of up to 760 times.

When the desired sample size has been reached, valve 40 is closed. The sixth valve 48 is opened and a seventh valve 62 is opened. When the partial pressure of hydrogen in the collection is in the range of 1 Torr, valve 48 is closed and valve 49 is opened which sweeps a reactive gas from the reactive gas source 46 through the diffusion space 22. The reactive gas reacts with the hydrogen on the surface of the hydrogen permeable membrane 18. Because of the low partial pressure of hydrogen, (less than 1 Torr), no explosion can occur in the diffusion space 22. However, the free hydrogen atoms on the surface of the hydrogen permeable membrane 18 can readily react with the $O_2$ forming OH and leave the surface of the hydrogen permeable membrane 18. This enables other hydrogen atoms to take a place the surface, which lowers the partial pressure of the hydrogen gas in the collection space 20. This drops the partial pressure of hydrogen gas in the collection space 20 to less than 5 millitorrs.

Although, the remaining impurities inevitably contain a small amount of hydrogen gas, it can be assumed as a worst case scenario that all the pressure of the gas being measured is from the impurities. Since the volume, pressure and temperature of the remaining impurities is known, the amount of impurities can be readily calculated. The amount of impurities can then be displayed or otherwise communicated to a systems administrator.

If the pressure of the impurities is very low, the identity of the actual impurities is irrelevant. However, over time, the amount of impurities may increase. At some point, the systems administrator may want to know the exact identity of the impurities to help pinpoint the source of the impurities. To identify the impurities, a residual gas analyzer chamber (RGA chamber) 54 is provided. The RGA chamber 54 is pumped to high vacuum by the vacuum turbo pump 28 and the vacuum backing pump 30. The pressure in the RGA chamber 54 is approximately $1 \times 10^{-6}$ Torr. An eighth valve 56 is opened and the remaining impurities are vented into the RGA chamber 54 for a measured period of time. The eighth valve 56 is then closed. The RGA chamber 54 has a much larger volume than does the calibrated section 50 of the network 24. As such, the pressure of the impurities decreases dramatically while the overall pressure of the RGA chamber 54 increases to approximately $2 \times 10^{-4}$ Torr. The vacuum turbo pump 28 and/or the scroll pump 30 are then run to decrease the pressure to approximately $2 \times 10^{-6}$ Torr. At this pressure, the RGA chamber 54 can be opened to the sample port of a secondary instrument 60, such as a quadripole mass spectrometer. The secondary instrument 60 can then analyze the actual impurities for element identification.

To reset the contamination level detection system 10, the hydrogen permeable membrane 18, the collection space 20, the calibrated section 50 of the network 24 and the RGA chamber 54 must be cleansed of impurities so that subsequent measurements of samples are accurate. To clean these components, the first valve 34 is opened to connect the hydrogen gas source 12 into the vacuum ballast 32 and into the diffusion space 22 of the hydrogen separator 16. The fifth and ninth valves 42 and 62 are closed. The hydrogen gas enters the diffusion space 22 and diffuses through the hydrogen permeable membrane 18 in reverse. This cleans the hydrogen permeable membrane 18. Any impurities dislodged from the hydrogen permeable membrane 18 flow into the collection space 20 along with the hydrogen gas crossing the hydrogen permeable membrane 18. This gas flows through the collection space 20, into the calibrated section 50, and into the RGA chamber 54. The gases are then drawn away and vented by the vacuum turbo pump 28 and the backing pump 30. By using the present invention contamination level detection system 10, accurate measurements can be obtained for contaminant levels as low as a few parts per billion. Furthermore, if the gas being sampled is highly pure, the present invention system 10 can be used to detect contamination as low as a few parts per trillion.

In the embodiment of FIG. 1, individual contaminants are identified using a secondary instrument 60, such as a mass spectrometer. However, contaminant gases such as nitrogen ($N_2$) and carbon monoxide (CO) have nearly identical masses. Thus, a mass spectrometer alone cannot accurately determine the individual amounts of such gases in the detected contaminants.

Figure 2:
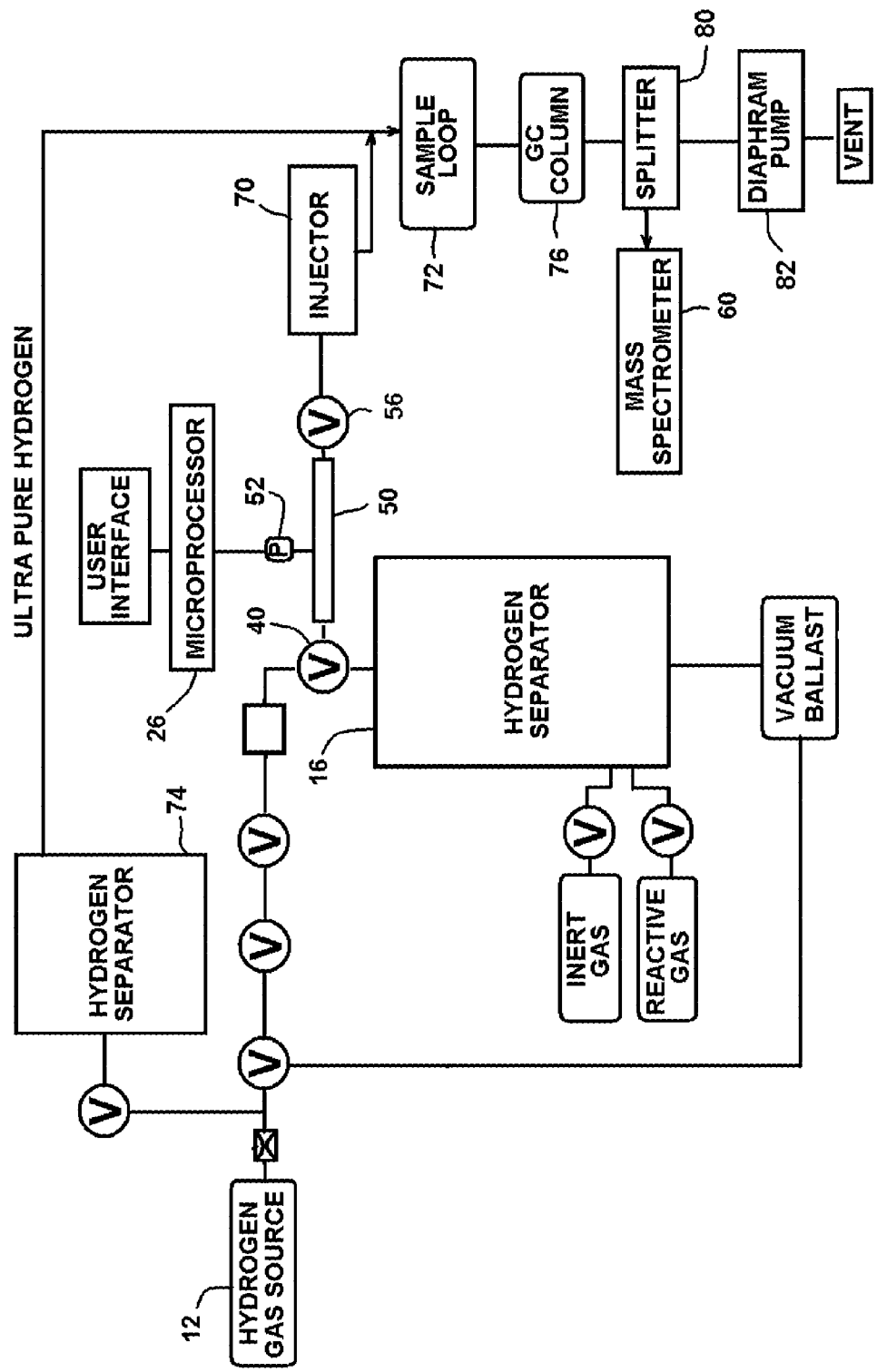
FIG. 2 is a block diagram schematic of the exemplary embodiment showing a subsystem for detecting contaminants that have similar molecular mass.

Referring to FIG. 2, it can be seen that the present invention has a subsystem for detecting contaminates having similar masses. If the systems administrator wants to know the exact identity of a specific set of impurities, the subsystem can be run.

An automated gas injector 70 is provided that is operated by the microprocessor 26. The injector 70 is loaded with the gas having concentrated impurities from the calibrated section 50 of the overall network. The calibrated section 50 is isolated and has a known volume. The pressure of the calibrated section 50 is known by the precision pressure gauge 52. The injector 70 has a known volume, therefore the pressure and volume of the sample that loads into the injector 70 can be readily calculated. The injector 70 injects the sample into a sample loop 72. The sample loop 72 mixes the sample with a carrier gas. The carrier gas is ultrapure hydrogen that is generated within the overall system. Gas from the original gas source 12 is directed into a second hydrogen separator 74. The second hydrogen separator 74 is separate and distinct from the first hydrogen separator 16. The second hydrogen separator 74 creates a stream of ultrapure hydrogen from the original gas source 12. The ultrapure hydrogen is fed into the sample loop 72 as a carrier gas.

In the sample loop 72, the injected sample mixes with the carrier gas. The sample loop 72 directs the gas mixture into a gas chromatography (GC) column 76. The GC column 76 enables different gases to pass through the GC column 76 at different rates. Consequently, if the impurities contain both $N_2$ and CO, these gases will pass through the GC column 76 at different rates even though these gases have nearly identical weights.

The gases exiting the GC column 76 are directed into a gas splitter 80 that is coupled to a pump 82. The splitter 80 lowers the pressure of the gas sample, by separating most of the carrier gas from the gas sample. The remaining gas sample is then directed to the mass spectrometer 60. The gases entering the mass spectrometer 60 produce measured peaks that are spaced in time due to the flow delays created by the GC column 76. Consequently, the mass spectrometer 60 can clearly differentiate between gases with similar weights, such as $N_2$ and CO because these gasses do not pass into the mass spectrometer 60 at the same time. From the above, it will be understood that three levels of results can be obtained for impurities. Using the pressure sensor 52, the microprocessor 26 alone can determine of the maximum level of contaminants. If contaminates are above or near threshold levels, the mass spectrometer 60 can be used to directly determine levels of contaminants having dissimilar weights. If results from the mass spectrometer indicate that contaminants of similar weight, such as N2 and CO, are present in significant amounts, then the subsystem of FIG. 2 can be run to separate the contaminates using a GC column 76. The result is that the systems administrator can identify when contamination becomes a problem.

It will be understood that the system and method that has been illustrated and described is merely exemplary and that a person skilled in the art can make many modifications to that embodiment. For instance, the shape of the network, the type of hydrogen separator and the position of many valves are a matter of design choice. All such variations, modifications and alternate embodiments are intended to be included within the scope of the present invention as defined by the claims.

What is claimed is:

1. A method of determining a concentration level for impurities in a gas sample that is mostly hydrogen, said method comprising the steps of:
   providing a hydrogen separator wherein a collection space and a diffusion space are separated by a hydrogen permeable membrane;
   filling said collection space with said gas sample, wherein said hydrogen permeates through said hydrogen permeable membrane into said diffusion space, therein providing said diffusion space with a partial pressure of hydrogen;
   sweeping said diffusion space with a sweep gas, therein lowering said partial pressure of hydrogen in said diffusion space;
   measuring a pressure in said collection space, wherein said pressure is indicative of said concentration level for said impurities in said gas sample; and
   removing said impurities from said collection space by introducing hydrogen into said diffusion space, wherein hydrogen diffuses through said hydrogen permeable membrane into said collection space to displace said impurities.

2. The method according to claim 1, further including a step of venting said diffusion space prior to said step of sweeping said diffusion space.

3. The method according to claim 1, further including a step of lowering said partial pressure of hydrogen pressure in said diffusion space with a vacuum pump.

4. The method according to claim 1, wherein said step of sweeping said diffusion space with a sweep gas includes sweeping said diffusion space with an inert gas that does not react with hydrogen.

5. The method according to claim 1, wherein said step of sweeping said diffusion space with a sweep gas includes sweeping said diffusion space with a reactive gas that does react with hydrogen.

6. The method according to claim 1, further including a step of identifying said impurities remaining in said collection space with a secondary instrument.

7. The method according to claim 6, wherein said step of identifying said impurities further includes the step of venting said collection space to a larger volume to create a lower pressure for said impurities that can be utilized as a test sample by said secondary instrument.

8. The method according to claim 6, further including steps of drawing said impurities into an injector, and injecting said impurities into said secondary instrument.

9. The method according to claim 6, further including a step of passing said impurities through a gas chromatography column prior to introducing said impurities into said secondary instrument.

10. The method according to claim 6, wherein said impurities are swept toward said secondary instrument with a carrier gas and said method further includes a step of using a splitter to separate most of said sweep gas from said impurities.

11. The method according to claim 10, further including a step of drawing gases from said collection space with at least one vacuum pump.

12. A method of determining a concentration level of impurities in a gas sample that is mostly hydrogen, said method comprising the steps of:
   providing a hydrogen separator having a collection space and a diffusion space separated by a hydrogen permeable membrane;
   introducing said gas sample into said collection space, wherein said hydrogen permeates through said hydrogen permeable membrane into said diffusion space, therein providing said diffusion space with a partial pressure of hydrogen and creating a first concentration of said impurities in said collection space;
   sweeping said diffusion space with an inert gas, therein further dropping said partial pressure of hydrogen in said diffusion space and creating a second concentration of said impurities in said collection space;
   sweeping said diffusion space with a reactive gas, therein still further lowering said partial pressure of hydrogen in said diffusion space;
   measuring a pressure in said collection space, wherein said pressure is indicative of said concentration level of total impurities in said gas sample.

13. The method according to claim 12, further including the step of identifying said impurities remaining in said collection space with a secondary instrument.

14. The method according to claim 13, further including the steps of drawing said impurities into an injector, compressing said impurities within said injector, and injecting said impurities into said secondary instrument.

15. The method according to claim 13, wherein said step of identifying said impurities further includes the step of venting said collection space to a second space where optical measuring techniques are utilized to quantify impurities.

16. The method according to claim 12, further including the step of providing a contaminant specific getter and removing at least one contaminant with said getter.

17. The method according to claim 16, wherein said step of removing said impurities includes introducing various getters into the collect space and absorbing particular contaminating gases for release at a later time.

18. The method according to claim 17 further including the step of drawing gases from said collection space with at least one vacuum pump.

* * * * *